(12) United States Patent
Hancock et al.

(10) Patent No.: US 7,745,123 B2
(45) Date of Patent: *Jun. 29, 2010

(54) CELL CYCLE REPORTING CELL LINE

(75) Inventors: Suzanne Hancock, Cardiff (GB); Simon Stubbs, Cardiff (GB); Nicholas Thomas, Cardiff (GB); Ellen Fanning, Nashville, TN (US); Jinming Gu, Boston, MA (US)

(73) Assignees: GE Healthcare UK Limited, Cardiff (GB); Vanderbilt University, Nashville, TN (US)

( * ) Notice: Subject to any disclaimer, the term of this patent is extended or adjusted under 35 U.S.C. 154(b) by 540 days.

This patent is subject to a terminal disclaimer.

(21) Appl. No.: 11/572,516

(22) PCT Filed: Jul. 22, 2005

(86) PCT No.: PCT/GB2005/002890

§ 371 (c)(1),
(2), (4) Date: Apr. 9, 2007

(87) PCT Pub. No.: WO2006/008547

PCT Pub. Date: Jan. 26, 2006

(65) Prior Publication Data

US 2007/0238144 A1 Oct. 11, 2007

Related U.S. Application Data

(60) Provisional application No. 60/590,814, filed on Jul. 23, 2004, provisional application No. 60/645,915, filed on Jan. 21, 2005, provisional application No. 60/645,968, filed on Jan. 21, 2005.

(51) Int. Cl.
  *C12Q 1/68* (2006.01)
(52) U.S. Cl. ..................... 435/6; 435/325; 435/252.3; 435/320.1; 536/23.1
(58) Field of Classification Search ..................... None
See application file for complete search history.

(56) References Cited

U.S. PATENT DOCUMENTS

| | | | |
|---|---|---|---|
| 4,683,202 A | 7/1987 | Mullis | |
| 5,288,641 A | 2/1994 | Roizman | |
| 6,048,693 A | 4/2000 | Bitter | |
| 6,159,691 A | 12/2000 | La Thangue et al. | |
| 7,235,401 B2 * | 6/2007 | Pines et al. | 435/320.1 |

FOREIGN PATENT DOCUMENTS

| | | |
|---|---|---|
| EP | 0 798 386 | 5/2004 |
| WO | WO03/031612 | 4/2003 |

OTHER PUBLICATIONS

Gu, J., et al., "Cell Cycle-dependent Regulation of a Human DNA Helicase that Localizes in DNA Damage Foci", Molecular Biology of the Cell, vol. 15, 2004, p. 3320-3332.

Filhol, O., et al., "Live-Cell Fluorescence Imaging Reveals the Dynamics of Protein Kinase CK2 Individual Subunits", Molecular and Cellular Biology, vol. 23, No. 3, 2003, p. 975-987.

Oakley, R., et al., "The Cellular Distribution of Fluorescently Labeled Arrestins Provides a Robust, Sensitive, and Universal Assay for Screening G Protein-Coupled Receptors", Assay and Drug Development Technologies, vol. 1, No. 1-1, 2002, p. 21-30.

Flatt, P., et al., "Mechanisms of Cell-Cycle Checkpoints: At the Crossroads of Carcinogenesis and Drug Discovery", Drug Metabolism Reviews, (2000), 32(3&4), 283-305.

Buolamwini, J., "Cell Cycle Molecular Targets in Novel Anticancer Drug Discovery", Current Pharmaceutical Design, (2000), 6, 379-392.

Barlogie, B., et al., "Flow Cytometry in Clinical Cancer Research", Cancer Research, (1983), 43(9), 3982-3997.

Pines, J., "Four-Dimensional Control of the Cell Cycle", Nature Cell Biology, (1999), 1, E73-E79.

Kohn, K., "Molecular Interaction Map of the Mammalian Cell Cycle Control and DNA Repair Systems", Molecular Biology of the Cell, (1999), 10, 2703-2734.

Herman, C., "Cytometric DNA Analysis in the Management of Cancer", Cancer, (1992), 69(6), 1553-1556.

Hauser, M., et al., "Histochemical Analysis of Root Meristem Activity in *Arabidopsis thaliana* Using a Cyclin:GUS (β-glucuronidase) Marker Line", Plant and Soil, (2000), 226, 1-10.

Brandeis, M., et al., "The Proteolysis of Mitotic Cyclins in Mammalian Cells Persists from the End of Mitosis Until the Onset of S Phase", The EMBO Journal, (1996), 15(19), 5280-5289.

Jones, J., et al., "Probing the Precision of the Mitotic Clock with a Live-Cell Fluorescent Biosensor", Nature Biotechnology, (2004), 22(3), 306-312.

Labas, Y., et al., "Diversity and Evolution of the Green Fluorescent Protein Family", PNAS, (2002), 99(7), 4256-4261.

Tsien, R., "The Green Fluorescent Protein", Annual Reviews Biochemistry, (1998), 67, 509-544.

Rittinger, K., et al., "Structural Analysis of 14-3-3 Phosphopeptide Complexes Identifies a Dual Role for the Nuclear Export Signal of 14-3-3 in Ligand Binding", Molecular Cell, (1999), 4, 153-166.

Jang, S., et al., "A Segment of the 5' Nontranslated Region of Encephalomyocarditis Virus RNA Directs Internal Entry of Ribosomes During In Vitro Translation", Journal of Virology, (1988), 62(8), 2636-2643.

(Continued)

*Primary Examiner*—Karen Cochrane Carlson
(74) *Attorney, Agent, or Firm*—Yonggang Ji

(57) ABSTRACT

The present invention relates to non-destructive and dynamic means for determining the cell cycle position of living cells. The invention provides stable cell lines which can be used to determine the cell cycle position, together with methods for measuring the effect of a test agent on the cell cycle position.

8 Claims, 3 Drawing Sheets

OTHER PUBLICATIONS

Sambrook, J., et al., Molecular Cloning—A Laboratory Manual, Cold Spring Harbor Laboratory Press, 1982.

Beaucage, S., et al., "Deoxynucleoside Phosphoramidites—A New Class of Key Intermediates for Deoxypolynucleotide Synthesis", Tetrahedron Letters, (1981), 22(20), 1859-1862.

Matthes, H., et al., "Simultaneous Rapid Chemical Synthesis of Over One Hundred Oligonucleotides on a Microscale", The EMBO Journal, (1984), 3(4), 801-805.

Saiki, R., et al., "Primer-Directed Enzymatic Amplification of DNA with a Thermostable DNA Polymerase", Science, (1988), 239, 487-491.

Tur-Kaspa, R., et al., "Use of Electroporation to Introduce Biologically Active Foreign Genes into Primary Rat Hepatocytes", Molecular and Cellular Biology, (1986), 6(2), 716-718.

Potter, H., et al., "Enhancer-dependent Expression of Human K Immunoglobulin Genes Introduced into Mouse pre-B Lymphocytes by Electroporation", (1984), 81, 7161-7165.

Graham, F., et al., "A New Technique for the Assay of Infectivity of Human Adenovirus 5 DNA", Virology, (1973), 52, 456-467.

Rippe, R., et al., "DNA-Mediated Gene Transfer into Adult Rat Hepatocytes in Primary Culture", Molecular and Cellular Biology, (1990), 10(2), 689-695.

Stewart, M., et al., "Gene Transfer In Vivo with DNA-Liposome Complexes: Safety and Acute Toxicity in Mice", Human Gene Therapy, (1992), 3, 267-275.

Torchilin, V., et al., "Targeted Accumulation of Polyethylene Glycol-Coated Immunoliposomes in Infarcted Rabbit Myocardium", FASEB J., (1992), 6, 2716-2719.

Zhu, N., et al., "Systematic Gene Expression After Intravenous DNA Delivery into Adult Mice", Science, (1993), 261, 209-211.

Ledley, F., "Somatic Gene Therapy for Human Disease: Background and Prospects", The Journal of Pediatrics, (1987), 110(1), 1-8.

Nicolau, C., et al., "In Vivo Expression of Rat Insulin after Intravenous Administration of the Liposome-Entrapped Gene for Rat Insulin I", PNAS, (1983), 80, 1068-1072.

Nicolau, C., et al., "Liposome-Mediated DNA Transfer in Eukaryotic Cells—Dependence of the Transfer Efficiency Upon the Type of Liposomes Used and the Host Cell Cycle Stage", Biochimica et Biophysica Acta, (1982), 721, 185-190.

Jiao, S., et al., "Particle Bombardment-Mediated Gene Transfer and Expression in Rat Brain Tissues", Biotechnology, (1993), 11, 497-502.

Miller, A., "Retroviral Vectors", Current Topics in Microbiology and Immunology, (1992), 158, 1-24.

Baichwal, V., et al., "Vectors for Gene Transfer Derived from Animal DNA Viruses: Transient and Stable Expression of Transferred Genes", in Gene Transfer, ed. R. Kucherlapati, New York, Plenum Press, (1986), 117-148.

Muzyczka, N., "Use of Adeno-Associated Virus as a General Transduction Vector for Mammalian Cells", Current Topics in Microbiology and Immunology, (1992), 158, 97-129.

Krasagakis, K., et al., "Growth and Characterization of a Cell Line from a Human Primary Neuroendocrine Carcinoma of the Skin (Merkel Cell Carcinoma) in Culture and as Xenograft", Journal of Cellular Physiology, (2001), 187(3), 386-391.

Paris, S., et al., "A Model of Spontaneous Lung Metastases Visualised in Fresh Host Tissue by Green Fluorescent Protein Expression", Clinical and Experimental Metastasis, (1999), 17(10), 817-822.

Pye, D., et al., "Dermal Fibroblasts Participate in the Formation of New Muscle Fibres when Implanted into Regenerating Normal Mouse Muscle", Journal of Anatomy, (2001), 198(Pt 2), 163-173.

Brod, S., et al., "Ingested Interferon-α Prevents Allograft Islet Transplant Rejection", Transplantation, (2000), 69(10), 2162-2166.

Terskikh, A., et al., "Fluorescent Timer: Protein that Changes Color with Time", Science, (2000), 290, 1585-1588.

Boyle, W., et al., "Phosphopeptide Mapping and Phosphoamino Acid Analysis by Two-Dimensional Separation on Thin-Layer Cellulose Plates", Methods in Enzymology, (1991), 201, 110-149.

Voitenleitner, C., et al., "Cell Cycle-Dependent Regulation of Human DNA Polymerase α-Primase Activity by Phosphorylation", Molecular and Cellular Biology, (1999), 19(1), 646-656.

Nelms, B., et al., "In Situ Visualization of DNA Double-Strand Break Repair in Human Fibroblasts", Science, (1998), 280, 590-592.

Van Den Bosch, M., et al., "The MRN Complex: Coordinating and Mediating the Response to Broken Chromosomes", EMBO Reports, (2003), 4(9), 844-849.

Gorlich, D., et al., "Transport Between the Cell Nucleus and the Cytoplasm", Annu. Rev. Cell Dev. Biol., (1999), 15, 607-660.

Hood, J., et al., "Diverse Nuclear Transport Pathways Regulate Cell Proliferation and Oncogenesis", Biochimica et Biophysica Acta, (2000), 1471, M31-M41.

Weis, K., "Regulating Access to the Genome: Nucleocytoplasmic Transport Throughout the Cell Cycle", Cell, (2003), 112, 441-451.

Fabbro, M., et al., "Regulation of Tumor Suppressors by Nuclear-Cytoplasmic Shuttling", Experimental Cell Research, (2003), 282, 59-69.

Hickson, I., "RecQ Helicases: Caretakers of the Genome", Nature Reviews, (2003), 3, 169-178.

Kalderon, D., et al., "A Short Amino Acid Sequence Able to Specify Nuclear Location", Cell, (1984), 39, 499-509.

Wolff, B., et al., "Leptomycin B is an Inhibitor of Nuclear Export: Inhibition of Nucleo-Cytoplasmic Translocation of the Human Immunodeficiency Virus Type 1 (HIV-1) Rev Protein and Rev-Dependent mRNA", Chemical Biology, (1997), 4, 139-147.

Kudo, N., et al., "Leptomycin B Inhibition of Signal-Mediated Nuclear Export by Direct Binding to CRM1", Experimental Cell Research, (1998), 242, 540-547.

Taneja, P., et al., "A Dominant-negative Mutant of Human DNA Helicase B Blocks the Onset of Chromosomal DNA Replication", The Journal of Biological Chemistry, (2002) 277(43), 40853-40861.

* cited by examiner

Figure 3a: Blue fluorescence (DNA)

Figure 3b: Green fluorescence (G2/M Cyclin B1–EGFP)

Figure 3c: Red fluorescence (G1/S PSLD-JRed)

US 7,745,123 B2

CELL CYCLE REPORTING CELL LINE

CROSS REFERENCE TO RELATED APPLICATIONS

This application is a filing under 35 U.S.C. §371 and claims priority to international patent application number PCT/GB2005/002890 filed Jul. 22, 2005, published on Jan. 26, 2006, as WO 2006/008547, which claims priority to U.S. provisional patent application Nos. 60/590,814 filed Jul. 23, 2004, 60/645,915 filed Jan. 21, 2005 and 60/645,968 filed Jan. 21, 2005; the disclosures of which are incorporated herein by reference in their entireties.

GOVERNMENT SUPPORT

This invention was made with government support under GM052948 awarded by the NIH. The government has certain rights in the invention.

TECHNICAL FIELD

The present invention relates to novel non-destructive and dynamic means for determining the cell cycle position of living cells.

BACKGROUND OF THE INVENTION

Eukaryotic cell division proceeds through a highly regulated cell cycle comprising consecutive phases termed G1, S, G2 and M. The two transition phases, G1 and G2, are interspersed between the DNA synthesis (S) phase in which cellular DNA is replicated and the mitosis (M) phase in which each cell divides to form two daughter cells.

Disruption of the cell cycle or cell cycle control can result in cellular abnormalities or disease states such as cancer which arise from multiple genetic changes that transform growth-limited cells into highly invasive cells that are unresponsive to normal control of growth. Transition of normal cells into cancer cells arises though loss of correct function in DNA replication and DNA repair mechanisms. All dividing cells are subject to a number of control mechanisms, known as cell-cycle checkpoints, which maintain genomic integrity by arresting or inducing destruction of aberrant cells. Investigation of cell cycle progression and control is consequently of significant interest in designing anticancer drugs (Flatt P M and Pietenpol J A 2000 Drug Metab Rev 32(3-4):283-305; Buolamwini J K 2000 Current Pharmaceutical Design 6, 379-392).

Accurate determination of cell cycle status is a key requirement for investigation of cellular processes which affect the cell cycle or are dependent on cell cycle position. Such measurements are particularly vital in drug screening applications where:

a) drugs which directly or indirectly modify cell cycle progression are desired, for example as anti-cancer treatments.
b) drugs are to be checked for unwanted effects on cell cycle progression.
c) it is suspected that an agent is active or inactive towards cells in a particular phase of the cell cycle.

Traditionally cell cycle status for cell populations has been determined by flow cytometry using fluorescent dyes which stain the DNA content of cell nuclei (Barlogie B et al. Cancer Res. 1983 43(9):3982-97). Flow cytometry yields quantitative information on the DNA content of cells and hence allows determination of the relative numbers of cells in, or the proportion of cells in, the G1, S and G2+M phases of the cell cycle. However this analysis is a destructive non-dynamic process and requires serial sampling of a population to determine cell cycle status with time. Furthermore standard flow cytometry techniques examine only the total cell population in the sample and do not yield data on individual cells which precludes study of cell cycle status of different cell types that may be present within the sample under analysis. Flow cytometry is therefore suitable for examining the overall cell cycle distribution of cells within a population but cannot be used to monitor the precise cell cycle status of an individual cell over time.

Consequently what is needed to study the effects of agents with desired or undesired effects on the cell cycle is a method to precisely determine cell cycle status of a single living cell by a non-destructive method that allows the same cell to be repeatedly interrogated over time. Furthermore it would be advantageous for cell cycle position to be determined from a probe controlled directly by cell cycle control components, rather than indirectly through DNA content or other indirect markers of cell cycle position as described above.

A number of methods have been described which make use of certain components of the cell cycle control mechanisms to provide procedures which analyse or exploit cell proliferation status.

U.S. Pat. No. 6,048,693 describes a method for screening for compounds affecting cell cycle regulatory proteins wherein expression of a reporter gene is linked to control elements which are acted on by cyclins or other cell cycle control proteins. In this method temporal expression of a reporter gene product is driven in a cell cycle specific fashion and compounds acting on one or more cell cycle control components may increase or decrease expression levels. Since the assay system contains no elements which provide for the destruction of the reporter gene product nor for destruction of any signal arising from the reporter gene, the method can not yield information on the cell cycle position of any cells in the assay and reports only on general perturbations of cell cycle control mechanisms.

WO 03/031612 describes DNA reporter constructs and methods for determining the cell cycle position of living mammalian cells by means of cell cycle phase-specific expression control elements and destruction control elements. One embodiment uses well characterised elements of the cell cycle control protein Cyclin B1 to control the expression and degradation of a green fluorescent protein (GFP) molecule to report cellular transition through G2 and M phases of the cell cycle. Since this construct is under the control of the Cyclin B1 promoter, GFP expression is absent during G1 and S thus preventing analysis of cells in these phases of the cell cycle.

A human helicase B homolog has been reported and characterised ((Taneja et al J. Biol. Chem., (2002), 277, 40853-40861). The report demonstrates that helicase activity is needed during G1 to promote the G1/S transition.

Gu et al (Mol. Biol. Cell., (2004), 15, 3320-3332) have shown that a small C-terminal region of the helicase B gene termed the phosphorylation-dependent subcellular localization domain (PSLD) is phosphorylated by Cdk2/cyclin E and contains NLS and NES sequences. Gu et al (Mol. Biol. Cell., (2004), 15, 3320-3332) carried out studies on cells that had been transiently transfected with plasmid encoding an EGFP-βGal-PSLD fusion (beta-galactosidase (βGal) was included in the construct as an inert group to make the whole fusion protein similar in size to the complete helicase B) expressed from a CMV promoter. Cells in G1 exhibited EGFP signal predominantly in the nucleus, whilst cells in other phases of the cell cycle exhibited predominantly cytoplasmic EGFP signal. These researchers concluded that the PSLD was directing translocation of the βGal-EGFP reporter from the nucleus to the cytoplasm around the G1/S phase transition of the cell cycle.

None of the preceding methods which use components of the cell cycle control mechanism provides means for readily and accurately determining the cell cycle status of an individual cell or a population of cells throughout the entire cell cycle. Accordingly a method has been developed and is herein described which uses key components of the cell cycle regulatory machinery, in defined combinations, to drive dual independent cellular reporters to provide novel means of determining cell cycle status at all phases of the cell cycle in individual living cells.

SUMMARY OF THE INVENTION

According to the first aspect of the invention, there is provided a stable cell line expressing:
i) a first polypeptide construct comprising a first detectable live-cell reporter molecule linked to at least one cell cycle phase-dependent location control element, the location of which construct within a mammalian cell is indicative of the cell cycle position; and
ii) a second polypeptide construct comprising a second detectable live cell reporter molecule linked to a destruction control element wherein said second reporter is detectable in a mammalian cell at a predetermined position in the cell cycle, wherein said first and second reporter molecules are distinguishable from each other and the stable cell line can be used to determine the cell cycle position.

The present invention provides cell lines containing polypeptide constructs which exhibit cell cycle phase specific activation, translocation or destruction of detectable reporter molecules by direct linkage of reporter signals to temporal and spatial expression, localisation and destruction of cell cycle components. This greatly improves the precision of determination of cell cycle phase status and allows continuous monitoring of cell cycle progression in individual cells. Furthermore the inventors have discovered that these key control elements can be isolated and abstracted from functional elements of the cell cycle control mechanism to permit design of cell cycle phase reporters which are dynamically regulated and operate in concert with, but independently of, endogenous cell cycle control components and hence provide means for monitoring cell cycle status without influencing or interfering with the natural progression of the cell cycle.

Suitably, the cell cycle phase-dependent location control element is selected from the group of peptides consisting of Rag2, Chaf1B, Fen1, PPP1R2, helicase B, sgk, CDC6 or motifs therein such as the phosphorylation-dependent subcellular localization domain of the C-terminal special control region of helicase B (PSLD).

Suitably, the destruction control element comprises the Cyclin B1 D-box.

Suitably, the first and second live-cell reporter molecules are selected from the group consisting of fluorescent protein and enzyme reporter.

Preferably, said fluorescent protein is selected from the group consisting of Green Fluorescent Protein (GFP), Enhanced Green Fluorescent Protein (EGFP), Emerald and J-Red. Preferably, said enzyme reporter is halo-tag (Promega).

Preferably, the first reporter molecule is EGFP and the second reporter molecule is J-Red, or the first reporter molecule is J-Red and the second reporter molecule is EGFP. More preferably, the first reporter molecule is J-Red and the second reporter molecule is EGFP.

In one preferred embodiment of the invention the first polypeptide construct comprises the phosphorylation-dependent subcellular localization domain of the C-terminal spatial control region of helicase B (PSLD) coupled to a red fluorescent protein (RFP), and the second polypeptide construct comprises 171 amino acids of the amino terminus of cyclin B1 coupled to a green fluorescent protein (GFP) expressed under the control of the cyclin B1 promoter.

When expressed in a mammalian cell these constructs exhibit cell cycle specific expression and destruction of the GFP construct and translocation of the RFP construct, with the GFP construct paralleling the expression and degradation of endogenous cyclin B1, and the RFP construct paralleling the translocation of endogenous Helicase B. Hence measurement of both GFP and RFP fluorescence intensity and localisation permits identification of cells in G1, S, G2 and M phases of the cell cycle. Analysis of the fluorescence characteristics of each cell in a population with time consequently yields dynamic information on the cell cycle status of each cell.

In further aspects of the invention there are provided methods for analysing cell cycle distribution of cultured cells and determining the effects of test agents on cell cycle distribution. The term 'test agent' should be construed as a form of electromagnetic radiation or as a chemical entity. Preferably, the test agent is a chemical entity selected from the group consisting of drug, nucleic acid, hormone, protein and peptide. The test agent may be applied exogenously to the cell or may be a peptide or protein that is expressed in the cell under study.

Thus, in a second aspect of the present invention, there is provided a method for determining the cell cycle position of a mammalian cell, said method comprising:
a) culturing a stable cell line as hereinbefore described; and
b) determining the cell cycle position by monitoring signals emitted by the first and second reporter molecules.

In a third aspect of the present invention, there is provided a method of determining the effect of a test agent on the cell cycle position of a mammalian cell, said method comprising:
a) culturing a stable cell line as hereinbefore described; and
b) determining the cell cycle position by monitoring signals emitted by the first and second reporter molecules wherein a difference between the emitted signals measured in the absence and in the presence of said test agent is indicative of the effect of the test agent on the cell cycle position of the cell.

In a fourth aspect of the present invention, there is provided a method of determining the effect of a test agent on the cell cycle position of a mammalian cell, said method comprising:
a) culturing a stable cell line as hereinbefore described;
b) determining the cell cycle position by monitoring signals emitted by the first and second reporter molecules; and
c) comparing the emitted signals in the presence of the test agent with a known value for the emitted signals in the absence of the test agent;

wherein a difference between the emitted signals measured in the presence of the test agent and said known value in the absence of the test agent is indicative of the effect of the test agent on the cell cycle position of the cell.

In yet a further aspect of the present invention methods are provided for determining the cell cycle dependencies of cellular processes by means of monitoring cellular processes in cells reporting the cell cycle position.

Thus, according to the fifth aspect of the present invention, there is provided a method of determining the effect of the mammalian cell cycle on a cellular process monitored by a process reporter which is known to vary in response to a test agent, said method comprising:
a) culturing a stable cell line as hereinbefore described;
b) determining the cell cycle position by monitoring signals emitted by the first and second reporter molecules; and
c) monitoring the signals emitted by the process reporter wherein the process reporter is distinguishable from the first and second reporter molecules;

wherein the relationship between cell cycle position determined by step b) and the signal emitted by the process reporter is indicative of whether or not the cellular process is cell cycle dependent.

DETAILED DESCRIPTION OF THE INVENTION

PSLD-RFP Construct

Figure 1:
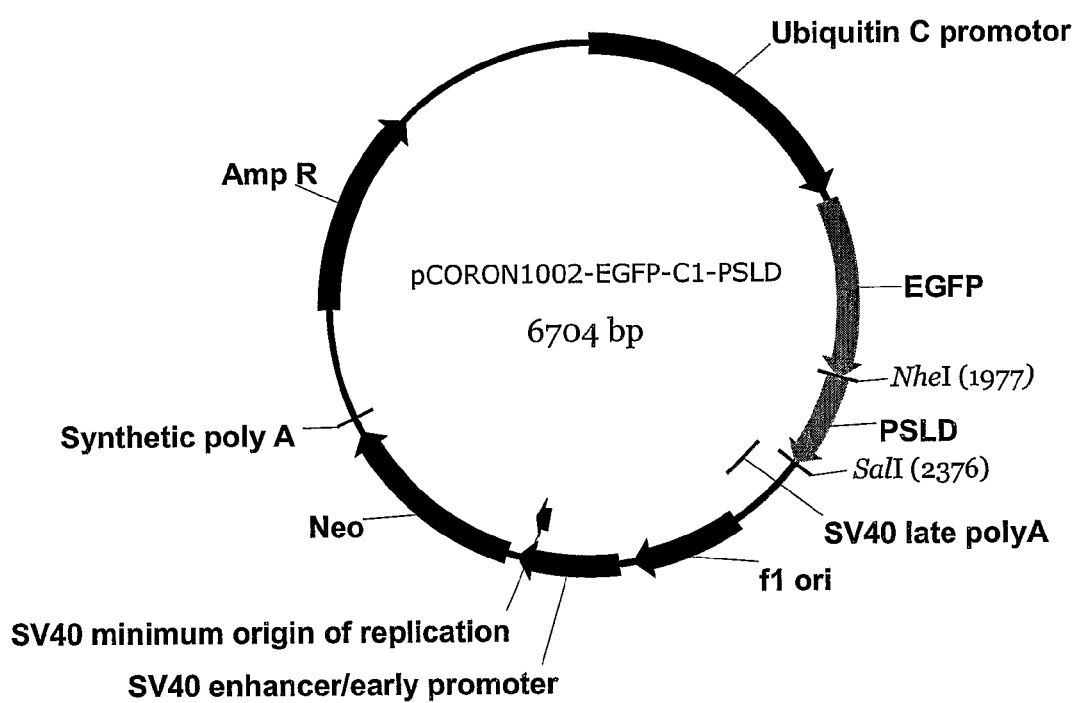
FIG. 1 is a vector map of pCORON1002-EGFP-C1-PSLD.
Figure 2B:
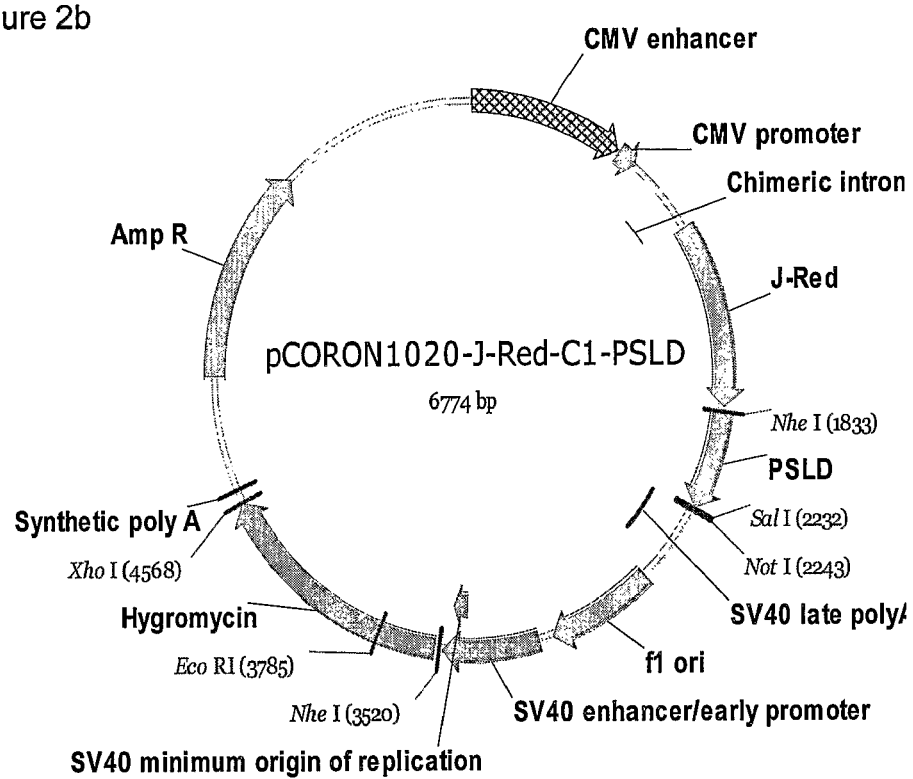
FIG. 2 shows vector maps of pCORON1022-JRed-C1-PSLD (FIG. 2a) and pCORON1020-JRed-C1-PSLD (FIG. 2b).
Figure 2A:
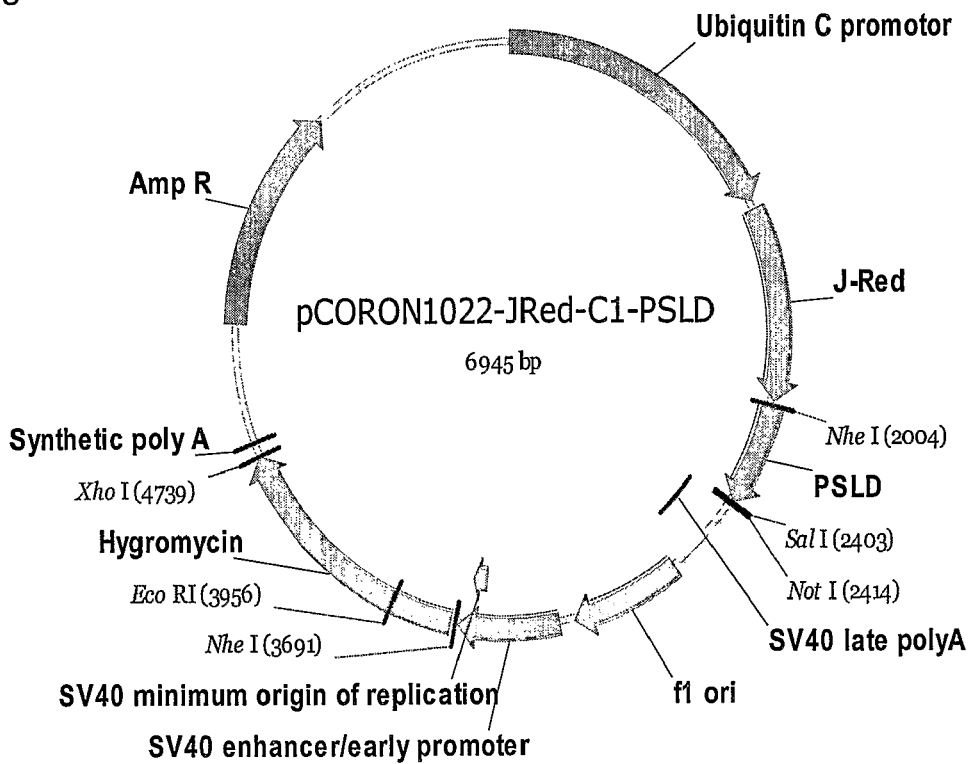

Full-length Human DNA helicase B (HDHB) cDNA was inserted as a BglII/NotI fragment (Taneja et al., J. Biol. Chem., (2002) 277, 40853-40861) into the NotI site of the pEGFP-C1 vector (Clontech). PCR amplification of the 390 by PSLD region and introduction of 5' NheI and 3' SalI restriction enzyme sites to the PSLD fragment were used to sub-clone into the vector pCORON1002-EGFP-C1 (GE Healthcare). The resulting 6704 by DNA construct pCORON1002-EGFP-C1-PSLD (FIG. 1), contains an ubiquitin C promoter, a bacterial ampicillin resistance gene and a mammalian neomycin resistance gene. Further modification of this vector was carried out using standard PCR and cloning techiques (Sambrook, J. et al (1989)) to replace the EGFP with the fluorescent protein J-Red (Evrogen), to convert the plasmid from the neomycin resistance to hygromycin resistance (FIG. 2a) and to replace the ubiquitin C promoter with CMV IE/promoter (FIG. 2b).

Dual Construct Stable Cell Line

A U2OS cell line stably expressing a Cyclin B1-EGFP cell cycle reporter (as described in WO03/031612 and supplied under product code 25-80-10 'G2M Cell Cycle Phase Marker' from Amersham Biosciences UK Limited/GE Healthcare Biosciences) was cultured according to the supplier's instructions. Cells were transfected with plasmids (FIGS. 2a and 2b) encoding the PSLD-RFP fusion protein (SEQ ID NO: 1) using Fugene (Roche) according to the manufacturer's instructions. Cells were placed under hygromycin (125 µg/ml) and neomycin (500 µg/ml) selection, and surviving clones selected for further expansion.

Imaging of Stable Cell Line Expressing G1/S and G2/M Sensors

A stable U2OS cell line expressing Cyclin B1-EGFP and PSLD-J Red fluorescent fusion proteins was grown in 96 well plates in McCoys medium supplemented with 10% serum under standard tissue culture conditions. Cells were fixed in 2% paraformaldehyde, stained with Hoechst, and imaged using an IN Cell Analyzer 1000 (GE Healthcare) with appropriate excitation and emission filters for blue (Hoechst), green (Cyclin B1-EGFP) and red (PSLD-J Red) fluorescence.

EXAMPLES

Below, the present invention will be explained in more detail by way of examples, which however are not to be construed as limiting the present invention as defined by the appended claims. All references given below and elsewhere in the present specification are hereby included herein by reference.

Example 1

Figure 3:
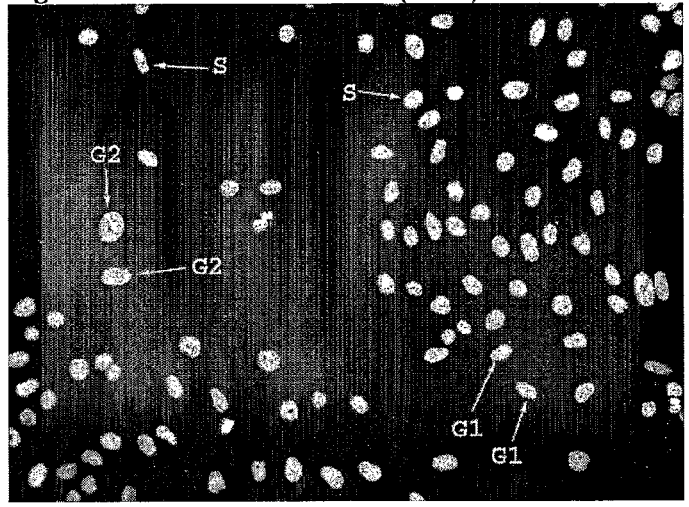
FIG. 3 presents images of U2OS cells expressing the cyclin B1-EGFP and the PSLD-J Red fluorescent proteins using an IN Cell Analyzer 1000 (GE Healthcare) imaging system. The cells are seen to be at varying stages of their cell cycle, as depicted by letters/numerals 'S', 'G1' and 'G2'. The presence of the Hoechst dye is indicated by the blue fluorescence in FIG. 3a, of expression of the G2/M Cyclin B1 green fluorescent protein reporter in FIG. 3b and the expression of the G1/S PSLD red fluorescent protein reporter in FIG. 3c.
Figure 3:
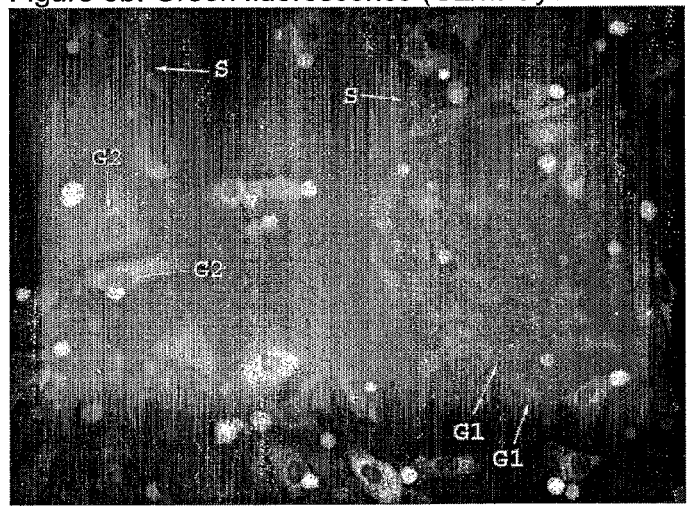
Figure 3:
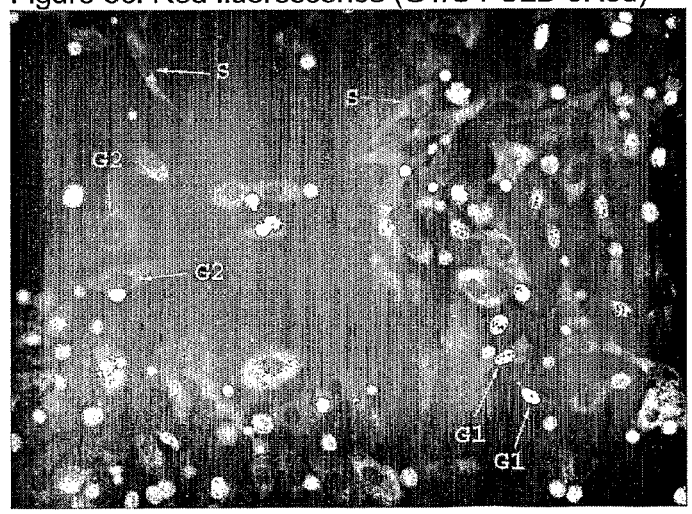

Images of the stable cell line cell line expressing Cyclin B1-EGFP and PSLD-J Red (FIG. 3) show differential expression and localisation of the green and red fusion proteins between cells in different phases of the cell cycle. Determination of the presence or absence of green and red fluorescent fusion proteins in the cytoplasm and nucleus of each cell allowed designation of cell cycle position according to the following scheme:

|  |  | G1 | S | G2 | M |
|---|---|---|---|---|---|
| Cytoplasm | Green | − | − | + | + |
|  | Red | − | + | + | + |
| Nucleus | Green | − | − | − | + |
|  | Red | + | − | − | + |

Experimental details relating to the production of stable cell lines expressing a polypeptide construct comprising a first detectable live-cell reporter molecule linked to at least one cell cycle phase-dependent location control element, the location of which construct within a mammalian cell is indicative of the cell cycle position, have been described in Applicant's copending U.S. provisional patent application US60/645,968 entitled "Cell Cycle Phase Markers", the disclosure of which is incorporated herein by reference in its entirety.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

What is claimed is:

1. A stable cell line expressing:
   i) a first polypeptide construct comprising a first detectable live-cell reporter molecule linked to at least one cell cycle phase-dependent location control element that is a cell cycle phase position motif which is the phosphorylation-dependent subcellular localization domain of the C-terminal special control region of helicase B (PSLD), wherein the location is indicative of the cell cycle position; and
   ii) a second polypeptide construct comprising a second detectable live cell reporter molecule such as an enzyme or fluorescent protein linked to a destruction control element that is the cyclin B1 D box, wherein said second reporter is detectable in a mammalian cell at a predetermined position in the cell cycle;
   wherein said first and second reporter molecules are chosen to be distinguishable.

2. The stable cell line of claim 1, wherein the first and second live-cell reporter molecules are selected from the group consisting of fluorescent protein and enzyme reporter.

3. The stable cell line of claim 2, wherein said fluorescent protein is selected from the group consisting of Green Fluorescent Protein (GFP), Enhanced Green Fluorescent Protein (EGFP), Emerald and J-Red.

4. The stable cell line of claim 2, wherein the first reporter molecule is EGFP and the second reporter molecule is J-Red, or the first reporter molecule is J-Red and the second reporter molecule is EGFP.

5. A method for determining the cell cycle position of a mammalian cell, said method comprising:
   a) culturing the stable cell line of claim 1; and
   b) determining the cell cycle position by monitoring signals emitted by the first and second reporter molecules.

6. A method for determining the effect of a test agent on the cell cycle position of a mammalian cell, said method comprising:
   a) culturing the stable cell line of claim 1; and
   b) determining the cell cycle position by monitoring signals emitted by the first and second reporter molecules wherein a difference between the emitted signals measured in the absence and in the presence of said test agent is indicative of the effect of the test agent on the cell cycle position of the cell.

7. A method for determining the effect of a test agent on the cell cycle position of a mammalian cell, said method comprising:
   a) culturing the stable cell line of claim 1;
   b) determining the cell cycle position by monitoring signals emitted by the first and second reporter molecules; and
   c) comparing the emitted signals in the presence of the test agent with a known value for the emitted signals in the absence of the test agent;
   wherein a difference between the emitted signals measured in the presence of the test agent and said known value in the absence of the test agent is indicative of the effect of the test agent on the cell cycle position of the cell.

8. A method for determining the effect of the mammalian cell cycle on a cellular process monitored by a process reporter which is known to vary in response to a test agent, said method comprising:
   a) culturing the stable cell line of claim 1;
   b) determining the cell cycle position by monitoring signals emitted by the first and second reporter molecules; and
   c) monitoring the signals emitted by the process reporter wherein the process reporter is distinguishable from the first and second reporter molecules;
   wherein the relationship between cell cycle position determined by step b) and the signal emitted by the process reporter is indicative of whether or not the cellular process is cell cycle dependent.

* * * * *

SEQUENCE LISTING

<160> NUMBER OF SEQ ID NOS: 3

<210> SEQ ID NO 1
<211> LENGTH: 385
<212> TYPE: PRT
<213> ORGANISM: Artificial Sequence
<220> FEATURE:
<223> OTHER INFORMATION: PSLD- J-RED fusion protein

<400> SEQUENCE: 1

```
Met Asp Glu Asp Gly Ser Glu Gly Gly Pro Ala Leu Phe Gln Ser Asp
1               5                   10                  15

Met Thr Phe Lys Ile Phe Ile Asp Gly Glu Val Asn Gly Gln Lys Phe
            20                  25                  30

Thr Ile Val Ala Asp Gly Ser Ser Lys Phe Pro His Gly Asp Phe Asn
        35                  40                  45

Val His Ala Val Cys Glu Thr Gly Lys Leu Pro Met Ser Trp Lys Pro
    50                  55                  60

Ile Cys His Leu Ile Gln Tyr Gly Glu Pro Phe Phe Ala Arg Tyr Pro
65                  70                  75                  80

Asn Gly Ile Ser His Phe Ala Gln Glu Cys Phe Pro Glu Gly Leu Ser
                85                  90                  95

Ile Asp Arg Thr Val Arg Phe Glu Asn Asp Gly Thr Met Thr Ser His
            100                 105                 110

His Thr Tyr Glu Leu Asp Gly Thr Cys Val Val Ser Arg Ile Thr Val
        115                 120                 125

Asn Cys Asp Gly Phe Gln Pro Asp Gly Pro Ile Met Arg Asp Gln Leu
    130                 135                 140

Val Asp Ile Leu Pro Asn Glu Thr His Met Phe Pro His Gly Pro Asn
145                 150                 155                 160

Ala Val Arg Gln Leu Ala Phe Ile Gly Phe Thr Thr Ala Asp Gly Gly
                165                 170                 175

Leu Met Met Gly His Phe Asp Ser Lys Met Thr Phe Asn Gly Ser Arg
            180                 185                 190

Ala Ile Lys Ile Pro Gly Pro His Phe Val Thr Ile Ile Thr Lys Gln
        195                 200                 205

Met Arg Asp Thr Ser Asp Lys Arg Asp His Val Cys Gln Arg Glu Val
    210                 215                 220

Thr Tyr Ala His Ser Val Pro Arg Ile Thr Ser Ala Ile Gly Ser Asp
225                 230                 235                 240

Glu Asp Ser Gly Leu Met Tyr Lys Gly Asn Gly Gly Asn Ala Ser Ser
                245                 250                 255

Gly Ala Pro Pro Ala Asp Phe Pro Ser Pro Arg Lys Ser Ser Gly Asp
            260                 265                 270

Ser Gly Gly Pro Ser Thr Pro Ser Ala Ser Pro Leu Pro Val Val Thr
        275                 280                 285

Asp His Ala Met Thr Asn Asp Val Thr Trp Ser Glu Ala Ser Ser Pro
    290                 295                 300

Asp Glu Arg Thr Leu Thr Phe Ala Glu Arg Trp Gln Leu Ser Ser Pro
305                 310                 315                 320

Asp Gly Val Asp Thr Asp Asp Leu Pro Lys Ser Arg Ala Ser Lys
                325                 330                 335

Arg Thr Cys Gly Val Asn Asp Asp Glu Ser Pro Ser Lys Ile Phe Met
            340                 345                 350
```

Val Gly Glu Ser Pro Gln Val Ser Ser Arg Leu Gln Asn Leu Arg Leu
    355                 360                 365

Asn Asn Leu Ile Pro Arg Gln Leu Phe Lys Pro Thr Asp Asn Gln Glu
    370                 375                 380

Thr
385

<210> SEQ ID NO 2
<211> LENGTH: 6945
<212> TYPE: DNA
<213> ORGANISM: Artificial Sequence
<220> FEATURE:
<223> OTHER INFORMATION: pCORON1022-JRed-C1-PSLD

<400> SEQUENCE: 2

| | | | | | |
|---|---|---|---|---|---|
| ggcctccgcg | ccgggttttg | gcgcctcccg | cgggcgcccc | cctcctcacg | gcgagcgctg | 60 |
| ccacgtcaga | cgaagggcgc | agcgagcgtc | ctgatccttc | cgcccggacg | ctcaggacag | 120 |
| cggcccgctg | ctcataagac | tcggccttag | aaccccagta | tcagcagaag | gacattttag | 180 |
| gacgggactt | gggtgactct | agggcactgg | ttttctttcc | agagagcgga | acaggcgagg | 240 |
| aaaagtagtc | ccttctcggc | gattctgcgg | agggatctcc | gtgggcggt | gaacgccgat | 300 |
| gattatataa | ggacgcgccg | ggtgtggcac | agctagttcc | gtcgcagccg | ggatttgggt | 360 |
| cgcggttctt | gtttgtggat | cgctgtgatc | gtcacttggt | gagtagcggg | ctgctgggct | 420 |
| ggccggggct | ttcgtggccg | ccgggccgct | cggtgggacg | gaagcgtgtg | gagagaccgc | 480 |
| caagggctgt | agtctgggtc | cgcgagcaag | gttgccctga | actggggtt | gggggagcg | 540 |
| cagcaaaatg | gcggctgttc | ccgagtcttg | aatggaagac | gcttgtgagg | cgggctgtga | 600 |
| ggtcgttgaa | acaaggtggg | gggcatggtg | ggcggcaaga | acccaaggtc | ttgaggcctt | 660 |
| cgctaatgcg | ggaaagctct | tattcgggtg | agatgggctg | gggcaccatc | tggggaccct | 720 |
| gacgtgaagt | ttgtcactga | ctggagaact | cggtttgtcg | tctgttgcgg | gggcggcagt | 780 |
| tatggcggtg | ccgttgggca | gtgcacccgt | acctttggga | gcgcgcgccc | tcgtcgtgtc | 840 |
| gtgacgtcac | ccgttctgtt | ggcttataat | gcagggtggg | gccacctgcc | ggtaggtgtg | 900 |
| cggtaggctt | ttctccgtcg | caggacgcag | ggttcgggcc | tagggtaggc | tctcctgaat | 960 |
| cgacaggcgc | cggacctctg | gtgaggggag | ggataagtga | ggcgtcagtt | tctttggtcg | 1020 |
| gttttatgta | cctatcttct | taagtagctg | aagctccggt | tttgaactat | gcgctcgggg | 1080 |
| ttggcgagtg | tgttttgtga | agttttttag | gcaccttttg | aaatgtaatc | atttgggtca | 1140 |
| atatgtaatt | ttcagtgtta | gactagtaaa | ttgtccgcta | aattctggcc | gttttttggct | 1200 |
| ttttttgttag | acgaagcttg | gtaccgagct | cgatatcgcc | accatggacg | aggatggttc | 1260 |
| agagggcggc | cccgccctgt | tccagagcga | catgaccttc | aaaatcttca | tcgacggcga | 1320 |
| ggtgaacggc | cagaagttca | ccatcgtggc | cgacggcagc | agcaagttcc | cccacggcga | 1380 |
| cttcaacgtg | cacgccgtgt | gcgagaccgg | caagctgccc | atgagctgga | agcccatctg | 1440 |
| ccacctgatc | cagtacggcg | agcccttctt | cgcccgctac | ccaacggca | tcagccactt | 1500 |
| cgcccaggag | tgcttccccg | agggcctgag | catcgaccgc | accgtgcgct | cgagaacga | 1560 |
| cggcaccatg | accagccacc | acaccctacga | gctggacgc | acctgcgtgg | tcagccgcat | 1620 |
| caccgtgaac | tgcgacggct | tccagcccga | cggccccatc | atgcgcgacc | agctggtgga | 1680 |
| catcctgccc | aacgagaccc | acatgttccc | ccacggcccc | aacgccgtgc | gccagctggc | 1740 |
| cttcatcggc | ttcaccaccg | ccgacggcgg | cctgatgatg | ggccacttcg | acagcaagat | 1800 |

-continued

```
gaccttcaac ggcagccgcg ccatcaagat ccccggcccc cacttcgtga ccatcatcac    1860
caagcagatg agggacacca gcgacaagcg cgaccacgtg tgccagcgcg aggtgaccta    1920
cgcccacagc gtgccccgca tcaccagcgc catcggtagc gacgaggatt ccggactcat    1980
gtacaagggc aatggcggca atgctagcag cggcgcacct ccagcagatt ttccgtcccc    2040
acggaagagc tctggagaca gtggaggacc cagcacaccg tcagcatctc cactccctgt    2100
agtcacagac cacgccatga caaatgatgt cacctggagc gaggcctctt cgcctgatga    2160
gaggacactc acctttgctg aaagatggca attatcttca cctgatggag tagatacaga    2220
tgatgattta ccaaaatcgc gagcatccaa aagaacctgt ggtgtgaatg atgatgaaag    2280
tccaagcaaa atttttatgg tgggagaatc tccacaagtg tcttccagac ttcagaattt    2340
gagactgaat aatttaattc ccaggcaact tttcaagccc accgataatc aagaaactta    2400
ggtcgacccg ggcggccgct tcgagcagac atgataagat acattgatga gtttggacaa    2460
accacaacta gaatgcagtg aaaaaaatgc tttatttgtg aaatttgtga tgctattgct    2520
ttatttgtaa ccattataag ctgcaataaa caagttaaca acaacaattg cattcatttt    2580
atgtttcagg ttcaggggga gatgtgggag gtttttttaaa gcaagtaaaa cctctacaaa    2640
tgtggtaaaa tccgataagg atcgatccgg gctggcgtaa tagcgaagag gcccgcaccg    2700 atcgccctt  ccaacagttg cgcagcctga atggcgaatg gacgcgccct gtagcggcgc    2760
attaagcgcg gcgggtgtgg tggttacgcg cagcgtgacc gctacacttg ccagcgccct    2820
agcgcccgct cctttcgctt tcttcccttc ctttctcgcc acgttcgccg gctttccccg    2880
tcaagctcta aatcggggc tcccttt agg gttccgattt agtgctttac ggcacctcga    2940
ccccaaaaaa cttgattagg gtgatggttc acgtagtggg ccatcgccct gatagacggt    3000
ttttcgccct tgacgttgg agtccacgtt ctttaatagt ggactcttgt tccaaactgg    3060
aacaacactc aaccctatct cggtctattc ttttgattta aagggattt tgccgatttc    3120 ggcctattgg ttaaaaaatg agctgattta acaaaaattt aacgcgaatt ttaacaaaat    3180
attaacgctt acaatttcct gatgcggtat tttctcctta cgcatctgtg cggtatttca    3240
caccgcatac gcggatctgc gcagcaccat ggcctgaaat aacctctgaa agaggaactt    3300
ggttaggtac cttctgaggc ggaaagaacc agctgtggaa tgtgtgtcag ttagggtgtg    3360
gaaagtcccc aggctcccca gcaggcagaa gtatgcaaag catgcatctc aattagtcag    3420
caaccaggtg tggaaagtcc ccaggctccc cagcaggcag aagtatgcaa agcatgcatc    3480
tcaattagtc agcaaccata gtcccgcccc taactccgcc catcccgccc ctaactccgc    3540
ccagttccgc ccattctccg ccccatggct gactaatttt ttttatttat gcagaggccg    3600
aggccgcctc ggcctctgag ctattccaga agtagtgagg aggcttttt ggaggcctag    3660 gcttttgcaa aaagcttgat tcttctgacg ctagcgatcg cccgggccac catgaaaaag    3720
cctgaactca ccgcgacgtc tgtcgagaag tttctgatcg aaaagttcga cagcgtctcc    3780
gacctgatgc agctctcgga gggcgaagaa tctcgtgctt tcagcttcga tgtaggaggg    3840
cgtggatatg tcctgcgggt aaatagctgc gccgatggtt tctacaaaga tcgttatgtt    3900
tatcggcact ttgcatcggc cgcgctcccg attccggaag tgcttgacat tggggaattc    3960
agcgagagcc tgacctattg catctcccgc cgtgcacagg gtgtcacgtt gcaagacctg    4020
cctgaaaccg aactgcccgc tgttctgcag ccggtcgcgg aggccatgga tgcgatcgct    4080
gcggccgatc ttagccagac gagcgggttc ggcccattcg gaccgcaagg aatcggtcaa    4140
```

```
tacactacat ggcgtgattt catatgcgcg attgctgatc cccatgtgta tcactggcaa    4200
actgtgatgg acgacaccgt cagtgcgtcc gtcgcgcagg ctctcgatga gctgatgctt    4260
tgggccgagg actgccccga agtccggcac ctcgtgcacg cggatttcgg ctccaacaat    4320
gtcctgacgg acaatggccg cataacagcg gtcattgact ggagcgaggc gatgttcggg    4380
gattcccaat acgaggtcgc caacatcttc ttctggaggc cgtggttggc ttgtatggag    4440
cagcagacgc gctacttcga gcggaggcat ccggagcttg caggatcgcc gcggctccgg    4500
gcgtatatgc tccgcattgg tcttgaccaa ctctatcaga gcttggttga cggcaatttc    4560
gatgatgcag cttgggcgca gggtcgatgc gacgcaatcg tccgatccgg agccgggact    4620
gtcgggcgta cacaaatcgc ccgcagaagc gcggccgtct ggaccgatgg ctgtgtagaa    4680
gtactcgccg atagtggaaa ccgacgcccc agcactcgtc cgagggcaaa ggaatagctc    4740
gagtttcgaa atgaccgacc aagcgacgcc caacctgcca tcacgatggc cgcaataaaa    4800
tatctttatt ttcattacat ctgtgtgttg gttttttgtg tgaatcgata gcgataagga    4860
tccgcgtatg gtgcactctc agtacaatct gctctgatgc cgcatagtta agccagcccc    4920
gacacccgcc aacacccgct gacgcgccct gacgggcttg tctgctcccg gcatccgctt    4980
acagacaagc tgtgaccgtc tccgggagct gcatgtgtca gaggttttca ccgtcatcac    5040
cgaaacgcgc gagacgaaag ggcctcgtga tacgcctatt tttataggtt aatgtcatga    5100
taataatggt ttcttagacg tcaggtggca cttttcgggg aaatgtgcgc ggaacccccta   5160
tttgtttatt tttctaaata cattcaaata tgtatccgct catgagacaa taaccctgat    5220
aaatgcttca ataatattga aaaggaagag tatgagtat tcaacatttc cgtgtcgccc    5280
ttattccctt ttttgcggca ttttgccttc ctgtttttgc tcacccagaa acgctggtga    5340
aagtaaaaga tgctgaagat cagttgggtg cacgagtggg ttacatcgaa ctggatctca    5400
acagcggtaa gatccttgag agttttcgcc ccgaagaacg ttttccaatg atgagcactt    5460
ttaaagttct gctatgtggc gcggtattat cccgtattga cgccgggcaa gagcaactcg    5520
gtcgccgcat acactattct cagaatgact tggttgagta ctcaccagtc acagaaaagc    5580
atcttacgga tggcatgaca gtaagagaat tatgcagtgc tgccataacc atgagtgata    5640
acactgcggc caacttactt ctgacaacga tcggaggacc gaaggagcta accgcttttt    5700
tgcacaacat gggggatcat gtaactcgcc ttgatcgttg ggaaccggag ctgaatgaag    5760
ccataccaaa cgacgagcgt gacaccacga tgcctgtagc aatggcaaca acgttgcgca    5820
aactattaac tggcgaacta cttactctag cttcccggca acaattaata gactggatgg    5880
aggcggataa agttgcagga ccacttctgc gctcggccct tccggctggc tggtttattg    5940
ctgataaatc tggagccggt gagcgtgggt ctcgcggtat cattgcagca ctggggccag    6000
atggtaagcc ctcccgtatc gtagttatct acacgacggg gagtcaggca actatggatg    6060
aacgaaatag acagatcgct gagataggtg cctcactgat taagcattgg taactgtcag    6120
accaagttta ctcatatata ctttagattg atttaaaact tcattttttaa tttaaaagga    6180
tctaggtgaa gatcctttt gataatctca tgaccaaaat cccttaacgt gagttttcgt    6240
tccactgagc gtcagacccc gtagaaaaga tcaaaggatc ttcttgagat cctttttttc    6300
tgcgcgtaat ctgctgcttg caaacaaaaa aaccaccgct accagcggtg gtttgtttgc    6360
cggatcaaga gctaccaact ctttttccga aggtaactgg cttcagcaga gcgcagatac    6420
caaatactgt tcttctagtg tagccgtagt taggccacca cttcaagaac tctgtagcac    6480
cgcctacata cctcgctctg ctaatcctgt taccagtggc tgctgccagt ggcgataagt    6540
```

-continued

| | |
|---|---|
| cgtgtcttac cgggttggac tcaagacgat agttaccgga taaggcgcag cggtcgggct | 6600 |
| gaacgggggg ttcgtgcaca cagcccagct tggagcgaac gacctacacc gaactgagat | 6660 |
| acctacagcg tgagctatga gaaagcgcca cgcttcccga agggagaaag gcggacaggt | 6720 |
| atccggtaag cggcagggtc ggaacaggag agcgcacgag ggagcttcca gggggaaacg | 6780 |
| cctggtatct ttatagtcct gtcgggtttc gccacctctg acttgagcgt cgattttgt | 6840 |
| gatgctcgtc agggggggcgg agcctatgga aaaacgccag caacgcggcc ttttacggt | 6900 |
| tcctggcctt ttgctggcct tttgctcaca tggctcgaca gatct | 6945 |

<210> SEQ ID NO 3
<211> LENGTH: 6774
<212> TYPE: DNA
<213> ORGANISM: Artificial Sequence
<220> FEATURE:
<223> OTHER INFORMATION: pCORON1020-JRED-C1-PSLD

<400> SEQUENCE: 3

| | |
|---|---|
| tcaatattgg ccattagcca tattattcat tggttatata gcataaatca atattggcta | 60 |
| ttggccattg catacgttgt atctatatca taatatgtac atttatattg gctcatgtcc | 120 |
| aatatgaccg ccatgttggc attgattatt gactagttat taatagtaat caattacggg | 180 |
| gtcattagtt catagcccat atatggagtt ccgcgttaca taacttacgg taaatggccc | 240 |
| gcctggctga ccgcccaacg accccccgcc cattgacgtc ataatgacgt atgttcccat | 300 |
| agtaacgcca atagggactt tccattgacg tcaatgggtg gagtatttac ggtaaactgc | 360 |
| ccacttggca gtacatcaag tgtatcatat gccaagtccg cccccctattg acgtcaatga | 420 |
| cggtaaatgg cccgcctggc attatgccca gtacatgacc ttacgggact ttcctacttg | 480 |
| gcagtacatc tacgtattag tcatcgctat taccatggtg atgcggtttt ggcagtacac | 540 |
| caatgggcgt ggatagcggt ttgactcacg gggatttcca gtctccaccc cattgacgt | 600 |
| caatgggagt ttgttttggc accaaaatca acgggacttt ccaaaatgtc gtaacaactg | 660 |
| cgatcgcccg ccccgttgac gcaaatgggc ggtaggcgtg tacggtggga ggtctatata | 720 |
| agcagagctc gtttagtgaa ccgtcagatc actagaagct ttattgcggt agtttatcac | 780 |
| agttaaattg ctaacgcagt cagtgcttct gacacaacag tctcgaactt aagctgcagt | 840 |
| gactctctta aggtagcctt gcagaagttg gtcgtgaggc actgggcagg taagtatcaa | 900 |
| ggttacaaga caggtttaag gagaccaata gaaactgggc ttgtcgagac agagaagact | 960 |
| cttgcgtttc tgataggcac ctattggtct tactgacatc cactttgcct ttctctccac | 1020 |
| aggtgtccac tcccagttca attacagctc ttaaggctag agtatcgcca ccatggacga | 1080 |
| ggatggttca gagggcggcc ccgccctgtt ccagagcgac atgaccttca aaatcttcat | 1140 |
| cgacggcgag gtgaacggcc agaagttcac catcgtggcc gacggcagca gcaagttccc | 1200 |
| ccacggcgac ttcaacgtgc acgccgtgtg cgagaccggc aagctgccca tgagctggaa | 1260 |
| gcccatctgc cacctgatcc agtacggcga gcccttcttc gcccgctacc caacggcat | 1320 |
| cagccacttc gcccaggagt gcttccccga gggcctgagc atcgaccgca ccgtgcgctt | 1380 |
| cgagaacgac ggcaccatga ccagccacca cacctacgag ctggacgca cctgcgtggt | 1440 |
| cagccgcatc accgtgaact gcgacggctt ccagcccgac ggccccatca tgcgcgacca | 1500 |
| gctggtggac atcctgccca acgagaccca catgttcccc cacggcccca acgccgtgcg | 1560 |
| ccagctggcc ttcatcggct tcaccaccgc cgacggcggc ctgatgatgg ccacttcga | 1620 |

-continued

```
cagcaagatg accttcaacg gcagccgcgc catcaagatc cccggccccc acttcgtgac    1680
catcatcacc aagcagatga gggacaccag cgacaagcgc gaccacgtgt gccagcgcga    1740
ggtgacctac gcccagcgcg tgccccgcat caccagcgcc atcggtagcg acgaggattc    1800
cggactcatg tacaagggca atggcggcaa tgctagcagc ggcgcacctc cagcagattt    1860
tccgtcccca cggaagagct ctggagacag tggaggaccc agcacaccgt cagcatctcc    1920
actccctgta gtcacagacc acgccatgac aaatgatgtc acctggagcg aggcctcttc    1980
gcctgatgag aggacactca cctttgctga agatggcaa ttatcttcac ctgatggagt    2040
agatacagat gatgatttac caaaatcgcg agcatccaaa agaacctgtg gtgtgaatga    2100
tgatgaaagt ccaagcaaaa tttttatggt gggagaatct ccacaagtgt cttccagact    2160
tcagaatttg agactgaata atttaattcc caggcaactt ttcaagccca ccgataatca    2220
agaaacttag gtcgacccgg gcggccgctt cgagcagaca tgataagata cattgatgag    2280
tttggacaaa ccacaactag aatgcagtga aaaaatgct ttatttgtga aatttgtgat    2340
gctattgctt tatttgtaac cattataagc tgcaataaac aagttaacaa caacaattgc    2400
attcatttta tgtttcaggt tcagggggag atgtgggagg tttttttaaag caagtaaaac    2460 ctctacaaat gtggtaaaat ccgataagga tcgatccggg ctggcgtaat agcgaagagg    2520
cccgcaccga tcgcccttcc caacagttgc gcagcctgaa tggcgaatgg acgcgccctg    2580
tagcggcgca ttaagcgcgg cgggtgtggt ggttacgcgc agcgtgaccg ctacacttgc    2640
cagcgcccta gcgcccgctc ctttcgcttt cttcccttcc tttctcgcca cgttcgccgg    2700
ctttccccgt caagctctaa atcgggggct ccctttaggg ttccgattta gtgctttacg    2760
gcacctcgac cccaaaaaac ttgattaggg tgatggttca cgtagtgggc catcgccctg    2820
atagacggtt tttcgccctt tgacgttgga gtccacgttc tttaatagtg gactcttgtt    2880
ccaaactgga acaacactca accctatctc ggtctattct tttgatttat aagggatttt    2940
gccgatttcg gcctattggt taaaaaatga gctgatttaa caaaaattta acgcgaattt    3000
taacaaaata ttaacgctta caatttcctg atgcggtatt ttctccttac gcatctgtgc    3060
ggtatttcac accgcatacg cggatctgcg cagcaccatg cctgaaata acctctgaaa    3120 gaggaacttg gttaggtacc ttctgaggcg gaaagaacca gctgtggaat gtgtgtcagt    3180
tagggtgtgg aaagtcccca ggctccccag caggcagaag tatgcaaagc atgcatctca    3240
attagtcagc aaccaggtgt ggaaagtccc caggctcccc agcaggcaga agtatgcaaa    3300
gcatgcatct caattagtca gcaaccatag tcccgcccct aactccgccc atcccgcccc    3360
taactccgcc cagttccgcc cattctccgc cccatggctg actaattttt tttatttatg    3420
cagaggccga ggccgcctcg gcctctgagc tattccagaa gtagtgagga gctttttttg    3480
gaggcctagg cttttgcaaa aagcttgatt cttctgacgc tagcgatcgc ccgggccacc    3540
atgaaaaagc ctgaactcac cgcgacgtct gtcgagaagt ttctgatcga aaagttcgac    3600
agcgtctccg acctgatgca gctctcggag ggcgaagaat ctcgtgcttt cagcttcgat    3660
gtaggagggc gtggatatgt cctgcgggta aatagctgcg ccgatggttt ctacaaagat    3720
cgttatgttt atcggcactt tgcatcggcc gcgctcccga ttccggaagt gcttgacatt    3780
ggggaattca gcgagagcct gacctattgc atctcccgcc gtgcacaggg tgtcacgttg    3840
caagacctgc ctgaaaccga actgcccgct gttctgcagc cggtcgcgga ggccatggat    3900
gcgatcgctg cggccgatct tagccagacg agcgggttcg gcccattcgg accgcaagga    3960
atcggtcaat acactacatg gcgtgatttc atatgcgcga ttgctgatcc ccatgtgtat    4020
```

-continued

```
cactggcaaa ctgtgatgga cgacaccgtc agtgcgtccg tcgcgcaggc tctcgatgag      4080
ctgatgcttt gggccgagga ctgccccgaa gtccggcacc tcgtgcacgc ggatttcggc      4140
tccaacaatg tcctgacgga caatggccgc ataacagcgg tcattgactg gagcgaggcg      4200
atgttcgggg attcccaata cgaggtcgcc aacatcttct tctggaggcc gtggttggct      4260
tgtatggagc agcagacgcg ctacttcgag cggaggcatc cggagcttgc aggatcgccg      4320
cggctccggg cgtatatgct ccgcattggt cttgaccaac tctatcagag cttggttgac      4380
ggcaatttcg atgatgcagc ttgggcgcag ggtcgatgcg acgcaatcgt ccgatccgga      4440
gccgggactg tcgggcgtac acaaatcgcc cgcagaagcg cggccgtctg gaccgatggc      4500
tgtgtagaag tactcgccga tagtggaaac cgacgcccca gcactcgtcc gagggcaaag      4560
gaatagctcg agtttcgaaa tgaccgacca agcgacgccc aacctgccat cacgatggcc      4620
gcaataaaat atctttattt tcattacatc tgtgtgttgg ttttttgtgt gaatcgatag      4680
cgataaggat ccgcgtatgg tgcactctca gtacaatctg ctctgatgcc gcatagttaa      4740
gccagccccg acaccgcca acaccgctg acgcgcctg acgggcttgt ctgctcccgg      4800
catccgctta cagacaagct gtgaccgtct ccgggagctg catgtgtcag aggttttcac      4860
cgtcatcacc gaaacgcgcg agacgaaagg gcctcgtgat acgcctattt ttataggtta      4920
atgtcatgat aataatggtt tcttagacgt caggtggcac ttttcgggga aatgtgcgcg      4980
gaacccctat ttgtttattt ttctaaatac attcaaatat gtatccgctc atgagacaat      5040
aaccctgata aatgcttcaa taatattgaa aaaggaagag tatgagtatt caacatttcc      5100
gtgtcgccct tattccctt tttgcggcat tttgccttcc tgtttttgct cacccagaaa      5160
cgctggtgaa agtaaaagat gctgaagatc agttgggtgc acgagtgggt tacatcgaac      5220
tggatctcaa cagcggtaag atccttgaga gttttcgccc cgaagaacgt tttccaatga      5280
tgagcacttt taaagttctg ctatgtggcg cggtattatc ccgtattgac gccgggcaag      5340
agcaactcgg tcgccgcata cactattctc agaatgactt ggttgagtac tcaccagtca      5400
cagaaaagca tcttacggat ggcatgacag taagagaatt atgcagtgct gccataacca      5460
tgagtgataa cactgcggcc aacttacttc tgacaacgat cggaggaccg aaggagctaa      5520
ccgctttttt gcacaacatg ggggatcatg taactcgcct tgatcgttgg gaaccggagc      5580
tgaatgaagc cataccaaac gacgagcgtg acaccacgat gcctgtagca atggcaacaa      5640
cgttgcgcaa actattaact ggcgaactac ttactctagc ttcccggcaa caattaatag      5700
actggatgga ggcggataaa gttgcaggac cacttctgcg ctcggccctt ccggctggct      5760
ggtttattgc tgataaatct ggagccgtg agcgtgggtc tcgcggtatc attgcagcac      5820
tggggccaga tggtaagccc tcccgtatcg tagttatcta cacgacgggg agtcaggcaa      5880
ctatggatga acgaaataga cagatcgctg agataggtgc ctcactgatt aagcattggt      5940
aactgtcaga ccaagtttac tcatatatac tttagattga tttaaaactt cattttaat      6000 ttaaaaggat ctaggtgaag atccttttg ataatctcat gaccaaaatc ccttaacgtg      6060
agttttcgtt ccactgagcg tcagacccg tagaaaagat caaaggatct tcttgagatc      6120 cttttttct gcgcgtaatc tgctgcttgc aaacaaaaaa accaccgcta ccagcggtgg      6180
tttgtttgcc ggatcaagag ctaccaactc ttttccgaa ggtaactggc ttcagcagag      6240
cgcagatacc aaatactgtt cttctagtgt agccgtagtt aggccaccac ttcaagaact      6300
ctgtagcacc gcctacatac ctcgctctgc taatcctgtt accagtggct gctgccagtg      6360
```

-continued

```
gcgataagtc gtgtcttacc gggttggact caagacgata gttaccggat aaggcgcagc    6420
ggtcgggctg aacggggggt tcgtgcacac agcccagctt ggagcgaacg acctacaccg    6480
aactgagata cctacagcgt gagctatgag aaagcgccac gcttcccgaa gggagaaagg    6540
cggacaggta tccggtaagc ggcagggtcg gaacaggaga gcgcacgagg gagcttccag    6600
ggggaaacgc ctggtatctt tatagtcctg tcgggtttcg ccacctctga cttgagcgtc    6660 gattttgtg  atgctcgtca gggggggcgga gcctatggaa aaacgccagc aacgcggcct   6720
ttttacggtt cctggccttt tgctggcctt ttgctcacat ggctcgacag atct          6774
```